United States Patent
Maxim

(10) Patent No.: US 10,908,156 B2
(45) Date of Patent: Feb. 2, 2021

(54) PORTABLE INSTRUMENT FOR IN VITRO DETECTION AND QUANTIFICATION OF BIOMARKERS

(71) Applicant: Nephrogen Inc., Palo Alto, CA (US)

(72) Inventor: Demetrios Samuel Maxim, Lexington, MA (US)

(73) Assignee: Nephrogen, Inc.

( * ) Notice: Subject to any disclaimer, the term of this patent is extended or adjusted under 35 U.S.C. 154(b) by 0 days.

(21) Appl. No.: 15/127,892

(22) PCT Filed: Mar. 20, 2015

(86) PCT No.: PCT/US2015/021855
§ 371 (c)(1),
(2) Date: Sep. 21, 2016

(87) PCT Pub. No.: WO2015/143387
PCT Pub. Date: Sep. 24, 2015

(65) Prior Publication Data
US 2017/0097344 A1    Apr. 6, 2017

Related U.S. Application Data

(60) Provisional application No. 61/968,813, filed on Mar. 21, 2014.

(51) Int. Cl.
*G01N 33/543*    (2006.01)
*G01N 35/02*     (2006.01)
*G01N 15/06*     (2006.01)
*G01N 1/28*      (2006.01)
(Continued)

(52) U.S. Cl.
CPC ........ *G01N 33/54386* (2013.01); *G01N 1/286* (2013.01); *G01N 15/0612* (2013.01); *G01N 21/272* (2013.01); *G01N 21/3103* (2013.01); *G01N 33/54393* (2013.01); *G01N 35/028* (2013.01); *G01N 21/253* (2013.01); *G01N 33/48707* (2013.01); *G01N 35/00* (2013.01); *G01N 2035/00356* (2013.01);
(Continued)

(58) Field of Classification Search
None
See application file for complete search history.

(56) References Cited

U.S. PATENT DOCUMENTS 5,316,726 A * 5/1994 Babson ............. G01N 35/0095
                                                  356/418
6,879,067 B1   4/2005 Rockwell
(Continued)

OTHER PUBLICATIONS

Active Motif "NR Sandwich AR ELISA," 2011, pp. 1-16 <www.activemotif.com/documents/105.pdf>.

*Primary Examiner* — Melanie Brown
(74) *Attorney, Agent, or Firm* — Paul B. Simboli; HelixIP LLP

(57) ABSTRACT

A portable assay instrument for rapid detection and quantification of biomarkers is described. The instrument may include components to automate steps of an assay. Assay-specific agitation during an incubation phase in which capture binding agents, detection binding agents, and conjugates are present in sample wells can appreciably increase the speed of the assay and improve assay sensitivity. The instrument may further include an optical detector and processor for automated probing of the sample wells and computation of biomarker concentration.

14 Claims, 7 Drawing Sheets

(51) Int. Cl.
G01N 21/27 (2006.01)
G01N 21/31 (2006.01)
G01N 35/00 (2006.01)
G01N 21/25 (2006.01)
G01N 33/487 (2006.01)

(52) U.S. Cl.
CPC ............ *G01N 2035/00524* (2013.01); *G01N 2800/245* (2013.01); *G01N 2800/347* (2013.01); *G01N 2800/7028* (2013.01)

(56) References Cited

U.S. PATENT DOCUMENTS

| | | | |
|---|---|---|---|
| 2002/0172621 A1* | 11/2002 | Barbera-Guillem | ......................... B01L 3/50853 422/503 |
| 2003/0108973 A1* | 6/2003 | Gatto-Menking | ... G01N 33/582 435/7.93 |
| 2007/0202538 A1* | 8/2007 | Glezer | .................. B01L 3/5025 435/7.1 |
| 2010/0184049 A1* | 7/2010 | Goodison | ............ C12Q 1/6886 435/6.11 |
| 2011/0203924 A1* | 8/2011 | Wohlstadter | .......... B01L 3/5085 204/403.01 |
| 2012/0046203 A1 | 2/2012 | Walsh et al. | |
| 2012/0190591 A1* | 7/2012 | Wohlstadter | .......... B01L 3/5085 506/39 |
| 2013/0065782 A1 | 3/2013 | Ostroff | |
| 2013/0109684 A1* | 5/2013 | Blagg | .................. C07D 233/26 514/230.5 |
| 2014/0138260 A1* | 5/2014 | Briman | ................. G01N 27/48 205/775 |

\* cited by examiner

PORTABLE INSTRUMENT FOR IN VITRO DETECTION AND QUANTIFICATION OF BIOMARKERS

CROSS REFERENCE TO RELATED APPLICATIONS

This application is for entry into the U.S. National Phase under § 371 for International Application No. PCT/US2015/021855 having an international filing date of Mar. 20, 2015, and from which priority is claimed under all applicable sections of Title 35 of the United States Code including, but not limited to, Sections 120, 363, and 365(c), and which in turn claims priority under 35 USC 119 to U.S. Patent Application No. 61/968,813 filed on Mar. 21, 2014.

FIELD

The embodiments relate to a portable, electro-mechanical apparatus and methods for biomarker or analyte detection and quantification. The apparatus may provide rapid and accurate quantification of biomarker concentrations in human or animal samples.

BACKGROUND

Biomarkers (e.g., proteins, microRNA's, messenger RNA etc.) and other analytes can aid in the diagnosis of and prognosis of many different kinds of diseases. Conventionally, biomarkers or analytes may be detected qualitatively with some user-friendly devices. One example of an easy-to-use device is a lateral-flow immunoassay, such as a pregnancy test. Although considered to be a gold standard for user-friendly immunoassays, a pregnancy test produces only a qualitative result.

Quantitative detection of biomarkers and analytes are typically carried out in laboratory settings. For example, a multi-step, enzyme-linked immunosorbent assay (ELISA) is a recognized gold standard for quantifying concentrations of biomarkers in samples. For small sample quantities (e.g., patient samples), an ELISA test may be performed at a laboratory by a skilled technician. For larger sample quantities, such as may be used in pharmaceutical screening, expensive and complex automation equipment may be used to run multiple qualitative and/or quantitative immunoassays in parallel. Although quantitative immunoassays such as ELISA can produce very reliable and accurate results, the results may not be available for hours or even days in most conventional tests.

SUMMARY

The inventor has recognized that some conventional assay tests for medical patients can be inconvenient to the patient and can involve an undesirably long amount of time before results are available. For example, an individual with a transplanted organ may, as part of preventative care, routinely travel to a doctor's office to provide a sample that can be sent to a laboratory for diagnostic testing. The laboratory may take hours or days before completing the test and returning results. It may then be necessary for the patient to make a follow-up call or a return visit to the doctor's office to discuss the results and take appropriate action.

In view of inconveniences posed by some conventional assay tests, the inventor has conceived of low-cost, portable instrumentation and associated methods of operation that may be used for rapid quantitative detection of biomarkers.

In some embodiments, the instrument automates, or semi-automates, an assay that targets detection of a particular biomarker. The automation can reduce human error in the assay (e.g., reduce the risk of contamination of an assay, human variability in executing assay steps, and/or mishandling or spills of assay components), and provide more reliable detection results. Actions that may be automated by the instrument include, but are not limited to, mixing or agitation of a sample during an incubation phase according to preset assay-specific guidelines, washing of a sample, controlling incubation times, adding a substrate and/or stop solution to the assay, optical illumination and/or reading of an assay, and calculation of a biomarker concentration level. The instrument may be the size of a desk-top printer, or smaller, and may be suitable for use in a physician's office, hospital lab, or residential dwelling.

The inventor has found that some assays (e.g., immunoassays or assays that bind assay components) can be accelerated by shaking the assay in a controlled manner during an incubation phase, and additionally by combining capture and detection binding agents (e.g., antibodies) in a prepared well prior to adding a sample. The combination of binding agents can eliminate one or more steps in some conventional immunoassay processes. With controlled shaking, combined binding agents, and semi-automation, the inventor has demonstrated that detection and quantification of vascular endothelial growth factor-C (VEGF-C), an indicator of chronic transplant rejection (CTR), can be completed in less than 30 minutes with a sensitivity of approximately 66 pg/mL. This time to completion can be more than 10 times faster than some conventional assays designed to detect the same biomarker, and the sensitivity can be within 40% of that achieved with conventional assays.

According to some embodiments, an instrument for detection and quantification of biomarkers, may comprising a sample holder configured to support at least two sample wells, and at least one motor and a sample platform arranged for moving the sample holder between two or more stations in the instrument. A first station may be a sample loading station. The instrument may further include an agitator located at an agitation station and configured to receive and couple to the sample holder, and a processor configured to activate the agitator, after receipt of the sample holder at the agitation station, for a preset assay-specific agitation period during an incubation phase of the assay. The incubation phase may initiate when a sample suspected to contain a target biomarker has been introduced into a solution in at least one of the sample wells. Further the solution may contain at least one detection binding agent for the target biomarker, and the at least one sample well may contain an immobilized binding agent. The instrument may further comprise an optical detector arranged to detect radiation from the at least one sample well, and the processor may be further configured to process a signal representative of the detected radiation to calculate a concentration of the target biomarker. In some aspects, the instrument may further include a display, wherein the processor is configured to display a value representative of the calculated concentration of the target biomarker on the display.

According to some aspects, the agitator comprises an orbital shaker having an armature of radius R, wherein a ratio of R to a diameter D of the at least one sample well is between approximately 1:2 and 2:1. In some implementations, the radius R is less than 10 mm. In some aspects, the agitation period is less than 10 minutes. A time from initiation of agitation and calculation of the target biomarker concentration may be no greater than 30 minutes.

In some implementations, an instrument for detection and quantification of biomarkers may further comprise a light source controlled by the processor and arranged to illuminate the at least one sample well. The optical detector may be arranged to detect light from the light source that is transmitted through the at least one sample well. According to some aspects, the light source comprises a first radiation source emitting at a first characteristic wavelength less than approximately 500 nm and a second radiation source emitting at a second characteristic wavelength greater than approximately 500 nm.

In some aspects, at least one detection binding agent in a solution in prepared sample wells comprises a detection antibody directed against the target biomarker. The solution may further include a conjugate that binds to the detection antibody. In some aspects, the target biomarker indicates renal transplant rejection or renal damage. In some aspects, the target biomarker indicates a presence of cancer.

According to some implementations, an instrument for detection and quantification of biomarkers may further comprise a dispenser having at least one dispensing tube and at least one valve controlled by a processor. The instrument (e.g., at least the processor and dispenser) may be configured to add solution from the dispenser into the at least one sample well and remove solution from the at least one sample well after an agitation period. In some implementations, the instrument may be configured to remove solution from at least one sample well by rotating the sample wells about an axis parallel to a plane of the solution surface in the sample wells at a rotation rate that dumps the solution from the sample wells without intermixing the solution between the sample wells.

Any of the foregoing aspects, implementations, and features may be used in one or more embodiments of an instrument for detection and quantification of biomarkers in any suitable combination. Additionally, any of the foregoing aspects, implementations, and features may be present in any method embodiment for operating an assay instrument as described below.

Method embodiments for operating an instrument for detection and quantification of biomarkers are also contemplated. According to some embodiments, a method for detecting and quantifying at least one biomarker in a sample may comprise acts of receiving, in a sample holder of an instrument, at least two prepared sample wells containing solution, wherein solution in at least one of the sample wells contains at least one detection binding agent for a target biomarker and the at least one sample well contains an immobilized binding agent. The method may further include acts of moving, with a motor, the sample holder between a first loading station of the instrument and a second station, and agitating, with an agitator, solution in the sample wells for a preset assay-specific agitation period during an incubation phase. In various aspects, a sample suspected to contain the target biomarker has been introduced into a solution in at least one of the sample wells prior to the incubation phase. The method may further comprise detecting, with an optical detector, radiation from the at least one sample well, and processing, with a processor, a signal representative of the detected radiation to calculate a concentration of the target biomarker. A method for detecting and quantifying at least one biomarker may further comprise displaying, by the processor on an electronic display, a value representative of the calculated concentration of the target biomarker.

According to some aspects, a method for detecting and quantifying at least one biomarker may comprise acts of illuminating, by a light source that is controlled by the processor, at least one sample well, and detecting, with the optical detector, light from the light source that is transmitted through the at least one sample well. In some implementations, the act of illuminating comprises exposing the at least one sample well to a first radiation having a first characteristic wavelength less than approximately 500 nm and a second radiation having a second characteristic wavelength greater than approximately 500 nm. In some aspects, the processing comprises calculating the concentration based upon a first signal detected for the first radiation and a second signal detected for the second radiation.

According to some implementations, a method for detecting and quantifying at least one biomarker may further comprise acts of removing solution from the at least one sample well after the agitation period, and adding, with a dispenser having at least one dispensing tube and at least one valve controlled by the processor, solution from the dispenser into the at least one sample well. In some aspects, the act of removing solution comprises rotating the sample wells about an axis parallel to a plane of the solution surface in the sample wells at a rotation rate that dumps the solution from the sample wells without intermixing the solution between the sample wells.

According to some embodiments, a method for detecting and quantifying at least one biomarker in a sample may comprise acts of receiving, in a sample holder of an automated assay instrument, at least two prepared sample wells containing solution, wherein solution in at least one of the sample wells contains at least one detection binding agent for a target biomarker and the at least one sample well contains an immobilized binding agent. The method may further comprise agitating, with an agitator of the instrument, solution in the sample wells for a preset assay-specific agitation period during an incubation phase, wherein a sample suspected to contain the target biomarker has been introduced into a solution in at least one of the sample wells prior to the incubation phase. In some aspects, the method includes detecting, with an optical detector of the instrument, radiation from the at least one sample well, and processing, with a processor, a signal representative of the detected radiation to calculate a concentration of the target biomarker.

In some implementations, a method for detecting and quantifying at least one biomarker may further comprise acts of exposing the at least one sample well to a first radiation having a first characteristic wavelength less than approximately 500 nm, and exposing the at least one sample well to a second radiation having a second characteristic wavelength greater than approximately 500 nm. The processing may comprise calculating the concentration based upon a first signal detected for the first radiation and a second signal detected for the second radiation.

Any of the foregoing features, aspects, and implementations of acts may be included in any suitable combination for an embodiment of a method of operating an instrument for detection and quantification of biomarkers.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

DETAILED DESCRIPTION

If diagnosed early enough, successful medical intervention may be initiated to minimize and ultimately cure many diseases, such as cancer and chronic transplant rejection (CTR). Biomarkers are often the most effective tools for the diagnosis of these diseases. Some biomarkers, however, have very specific diagnostic cutoff levels for differentiating between diseased and non-diseased states of an individual. Although conventional enzyme-linked immunosorbent assay (ELISA) tests may be accurate, robust, and quantitative techniques for determining biomarker concentrations in bodily fluids, they typically lack the speed needed for convenient medical diagnostic testing. Embodiments described herein include a portable, inexpensive, assay instruments that can rapidly and accurately quantify biomarker concentrations in samples. According to some embodiments, an assay instrument is 11 times faster than multi-step ELISA techniques, over 10 times less expensive than current commercial instruments, and can detect protein concentrations as low as 31 pg/mL in human blood plasma.

Figure 1A:
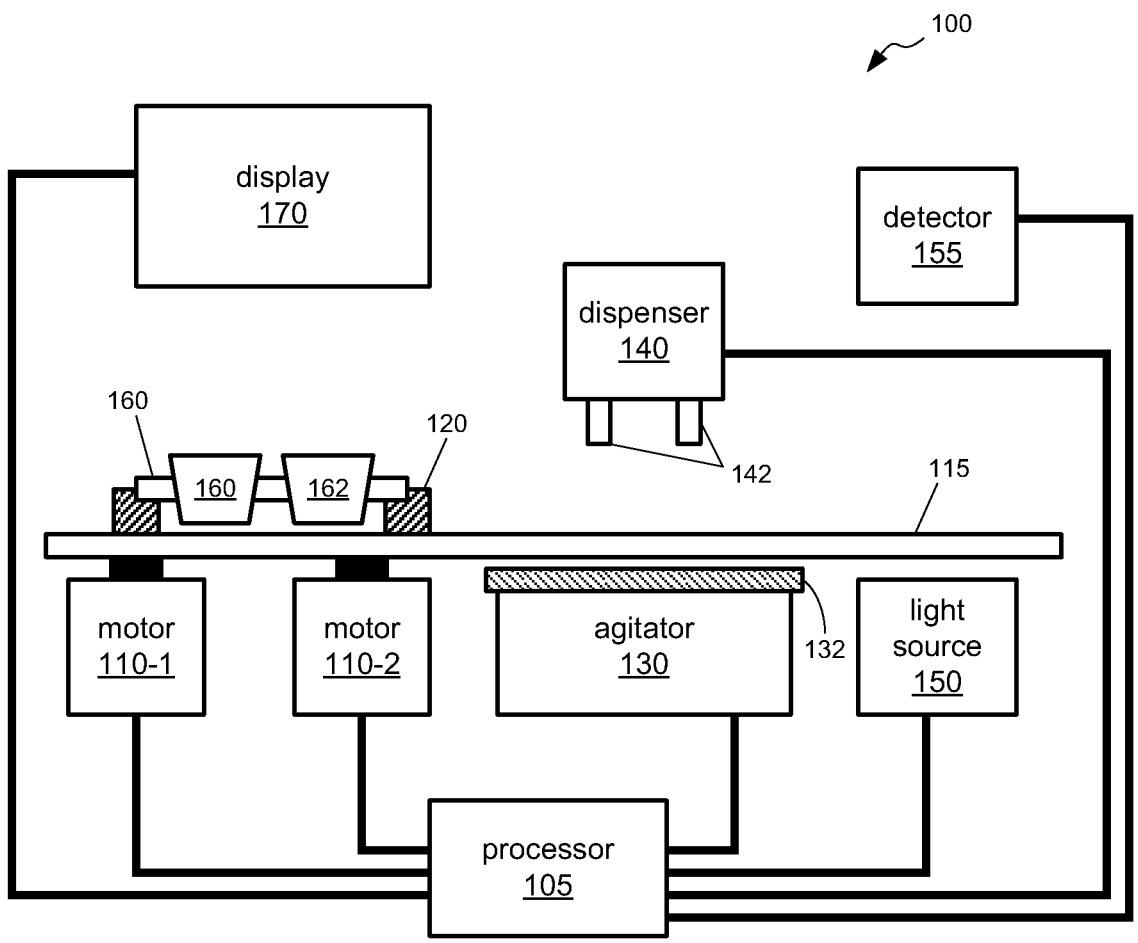
FIG. 1A depicts some components of a portable instrument for in vitro detection and quantification of biomarkers, according to some embodiments.

In overview, a non-limiting embodiment of a portable assay instrument 100 for in vitro detection and quantification of biomarkers is depicted in FIG. 1A. An instrument 100 may comprise a sample plate 160 comprising at least two sample wells 162, 164. The sample wells may be mountable in the sample plate, and may receive a fluid sample to be assayed. The instrument 100 may further include a sample platform 115 that supports and allows for positioning of the sample holder 120, and one or more motors 110-1, 110-2 arrange to move the sample holder 120.

The instrument 100 may further include a processor 105 (e.g., a microprocessor or microcontroller) that is configured to control the stepper motors as well as other components of the instrument. For example, the processor may also control an agitator 130 that shakes or agitates the sample wells during an incubation phase of an assay. In some embodiments, an assay instrument includes a light source 150 that may be controlled by the processor to probe the sample wells after completion of the assay. An assay instrument 100 may further include a fluid dispenser 140 to administer rinse solutions, sample, substrate, and/or stop solution to the sample wells during the course of an assay. An assay instrument 100 may also include an optical detector 155 that is arranged to detect light from and/or transmitted through the sample wells.

An assay instrument may further include an electronic display 170. Information about operation of the instrument 100 or results of an assay may be displayed on the display 170 during operation of the instrument. In some embodiments, the display may comprise a touch screen and provide a user-interface for operation of the instrument. In some implementations, an assay instrument may include buttons, a keyboard, or other user interface devices for operating the instrument.

In further detail, the sample plate 160 may be mountable on a sample holder 120. For example, the sample holder may receive the sample plate in a secure manner. In some implementations, the sample plate may include magnetic material, and the sample holder may include electromagnets that can be switched on to secure the sample plate. According to some embodiments, the sample holder 120 may be positioned and/or rotated by one or more motors 110-1, 110-2 that are controlled by instructions from the processor 105. In some embodiments, the sample wells and sample holder may be moved on the platform 115 to different stations (e.g., an agitation station, a sample-loading station, a dispensing station, an optical detection station, a solution decanting station) during the course of an assay.

Processor 105 may be any suitable processor such as a microprocessor or microcontroller that can be programmed with machine-readable instructions to execute various actions for controlling the portable assay instrument 100. For example, the processor 105 may be an Arduino UNO R3 microcontroller board available through an on-line web site http://store.arduino.cc. In some embodiments, a processor 105 may not be included with the portable instrument. For example, the processor may be a processor of a laptop computer, smart phone, or other computing device that may be interfaced to the portable assay instrument 100.

The display 170 may be any suitable visual display. For example, the display may comprise a touch screen display, an LCD display, a plasma display, or a cathode ray tube display in some embodiments. In some implementations, a portable instrument 100 may not include a display, and the display may instead be included with a laptop or other computing device that is interfaced with the instrument.

The motors 110-1, 110-2 may be any suitable stepper motor that can be controlled by a digital input waveform and/or other signal provided by a processor 105, for example. In some embodiments, the speed and/or the number of rotations or a partial rotation of a stepper motor can be controlled to selected values by signals from a processor 105. An example of the stepper motor is a NEMA 8-size bipolar stepper motor (Item #: 1204), available from Polulu Electronics of Las Vegas, Nev. The motors may be mechanically coupled to the sample holder 120. In some implementations, induction motors may be used, e.g., DC or AC motors. Additionally, a transmission, gearing mechanism, and/or pulleys may be used between a motor drive and object that is driven by the motor.

Dispenser 140 may be configured to receive one or more fluid supplies from which fluids may be dispensed to the sample wells 162, 164. For example, the dispenser 140 may include or receive one or more reservoirs for rinse solution, substrate, and or stop solution. In some implementations, the dispenser may include or receive reservoirs for one or more samples to be tested. Additional reservoirs may also be included or received for solutions of detection binding agents and conjugate. The reservoirs may be consumable items that are loaded into and removed from the dispenser. The dispenser 140 may further include electromechanical fluidic valves that control an amount of fluid dispensed from each reservoir. In some implementations, a dispenser comprises a peristaltic pump. An example of a peristaltic pump is a Series 100 micro peristaltic pump available from the Williamson Manufacturing Company located at Poynings, West Sussex, England. The valves may be controlled by signals sent by the processor 105 to dispense a measured amount of fluid to a respective sample well. In some embodiments, a dispenser 140 may include one or more dispensing nozzles 142 that are spaced apart by a distance that is approximately equal to the spacing of the sample wells.

A light source 150 may comprise one or more sources of optical radiation that emit light at one or more characteristic wavelengths. In some embodiments, a light source may comprise a white light source, an arc lamp source, one or more light-emitting diodes (LEDs), one or more laser diodes, or any suitable laser. In one embodiment of the invention, the light source comprises a tungsten lamp and appropriate filters for transmitting specific wavelengths of light that are selected for one or more detection components of an assay. In one embodiment of the invention, the light source consists of a xenon bulb instead of a tungsten lamp. According to some embodiments, ambient light may be used as a light source. An example light source is a 447.5 nm LUXEON Rebel LED (part number: LXML-PR01-0500) from LUXEON. In some implementations, a light source 150 may include optical components such as lenses, polarization filters, optical density filters, and or diffusers. In some embodiments, an optical component comprises a 6° 15 mm circular beam optic (part number: 180) available from Polymer Optics of Wokingham, Berkshire, England. The light source 150 may be arranged to illuminate one or more sample wells at a time. A light source may be controlled by signals issued from the processor 105 (e.g., turn on to probe a sample well, and subsequently turn off). When a single sample well is probed at a time, a stepper motor may move the sample wells with respect to the light source so that the sample wells can be probed sequentially.

The detector 155 may comprise one or more optical detectors. A detector may convert an optical intensity received at the detector into an electrical signal that can be transmitted to and processed by the processor 105. Any suitable detector 155 may be used to detect light from the sample wells. In some implementations, a detector 155 may be a photodiode or avalanche photodiode. In some cases, a detector may be an active pixel sensor (APS). In one embodiment of the invention, a detector 155 is a photomultiplier tube. In another embodiment, the detector may be a light-dependent resistor or phototransistor.

In some implementations, an agitator may comprise an orbital shaker, vortex shaker, or vibrator. For example, a plate 132 of the agitator, to which the sample plate 160 may be secured, may be shaken or vibrated by the agitator. In some implementations, a motor and armature may couple to the plate 132 to move the plate in an orbit. In some embodiments, at least one vibrator may couple to the plate 132. Vibrations may be induced in the plate by the vibrator, which then couple to the sample wells. A vibrator may be mechanical (e.g., a motor coupled to the plate and rotating an out-of-balance attachment that excites vibrations in the plate), electromagnetic (e.g., a coil and magnet or speaker assembly that excites vibrations in the plate), or an ultrasonic transducer that excites ultrasonic vibrations in the plate 132.

During operation of an assay instrument 100, prepared sample wells 162, 164 may contain solution having capture and/or immobilizing binding agents and detection binding agents. A sample from a patient may be added to the sample wells. The wells and sample plate 160 may be secured in the sample holder 120, and moved by a stepper motors 110-1 to or from the agitator 130, according to some embodiments. Electromagnets on the agitator 130 may engage the sample holder 120 or sample plate 160 and shake or otherwise agitate the solutions in the sample wells during an incubation phase of the assay. The agitation may continue at a preset level for a preset amount of time.

The preset agitation conditions during the incubation phase may be determined from prior studies to be conditions that decrease the length of time that the assay takes to complete and to improve the sensitivity of the assay. The preset agitation conditions may be assay-specific, and may be programmed into a memory device of the assay instrument. Agitation during incubation of the assay may last between 1 minute and 30 minutes depending on a type of assay. In some embodiments, the agitation and incubation phase is less than 15 minutes. In some embodiments, the agitation and incubation phase is less than 10 minutes.

After agitation, the sample plate 160 may be moved by the stepper motors to a dumping station, not shown in the drawing, and the solution may be removed from the sample wells. The sample wells may then be moved by the stepper motor to the dispenser 140, where a rinsing solution may be added to the wells. Subsequently, the sample wells may be returned to the dumping station where the rinsing solution is removed from the wells. The acts of rinsing adding rinsing solution and removing rinsing solution may be repeated several times.

The sample wells may next be returned to the dispenser 140 where a substrate is added to the sample wells. After a substrate incubation time, a stop solution may be added by the dispenser, and the sample wells may be moved to the detector 155 where radiation from the sample wells are detected and converted to electrical signals for transmission to the processor 105. The processor may be received the electrical signals and determine an optical property (e.g., color of light, intensity of light, absorbance of light by the wells) of the sample wells. From the measured property, the processor may compute a concentration of a target biomarker present in the patient sample and display a result on display 170.

Figure 1B:
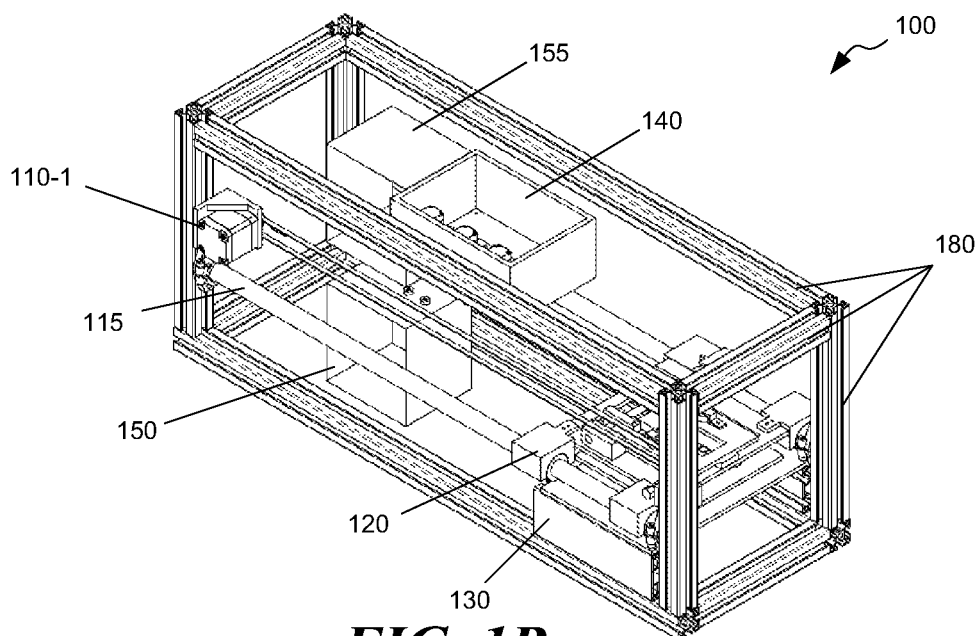
FIG. 1B illustrates a portable instrument for in vitro detection and quantification of biomarkers, according to some embodiments.

An implementation of a prototype portable assay instrument 100 is illustrated in FIG. 1B. The prototype instrument measures approximately 1 foot in height, 1 foot in depth, and approximately 2 feet in length, though substantial reduction in size can be achieved with further refinements of the design. With further refinements, the assay instrument may be the size of a desk-top printer or smaller. The prototype instrument includes a frame 180 that supports a stepper motor 110-1 configured to move the sample holder 120 back and forth on a sample platform 115 comprising parallel rails. The frame 180 also supports an agitator 130, dispenser 140, light source assembly 150, and detector assembly 155. The frame could be covered with opaque panels (not shown) to shield the assay and detection optics from ambient light and/or contaminants.

Figure 1C:
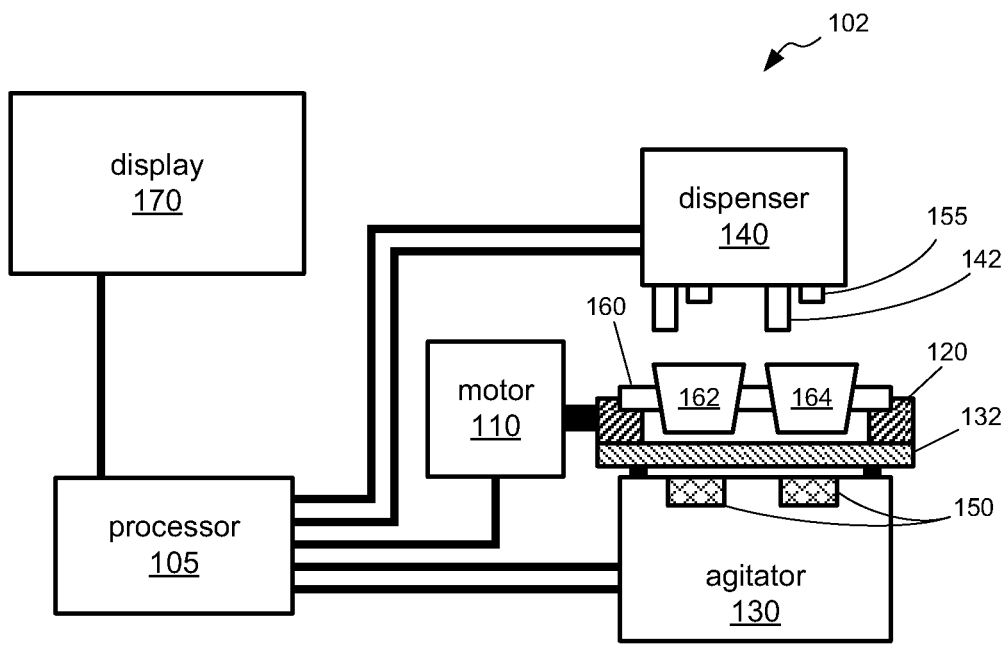
FIG. 1C depicts some components of a portable instrument for in vitro detection and quantification of biomarkers, according to some embodiments.

FIG. 1C depicts another embodiment of a portable assay instrument 102 for in vitro detection and quantification of biomarkers. Similar components from the embodiment shown in FIG. 1A are identified with same numbers, and their descriptions are not repeated. According to some embodiments, a portable assay instrument 102 may not include a platform 115 across which a sample holder 120 and sample wells 162, 164 are moved. Instead, the sample wells may only be moved during loading and unloading and during agitation. According to some embodiments, solutions may be removed from the sample wells by aspiration through additional tubes 142 introduced into the wells by the dispenser, for example. Alternatively, the sample plate 160 may be ejected by a motor 110 and drive assembly from the instrument 102 for solution removal. For example, an individual may dump solutions and rinses from the sample wells into a waste reservoir after the plate is ejected, and reinsert the sample plate 160 for further processing. According to some embodiments, a light source 150 (e.g., one or more LEDs) may be incorporated on a platform or plate of the agitator 130, and a detector 155 (e.g., one or more photodiodes) may be incorporated with the dispenser 140.

Figure 2:
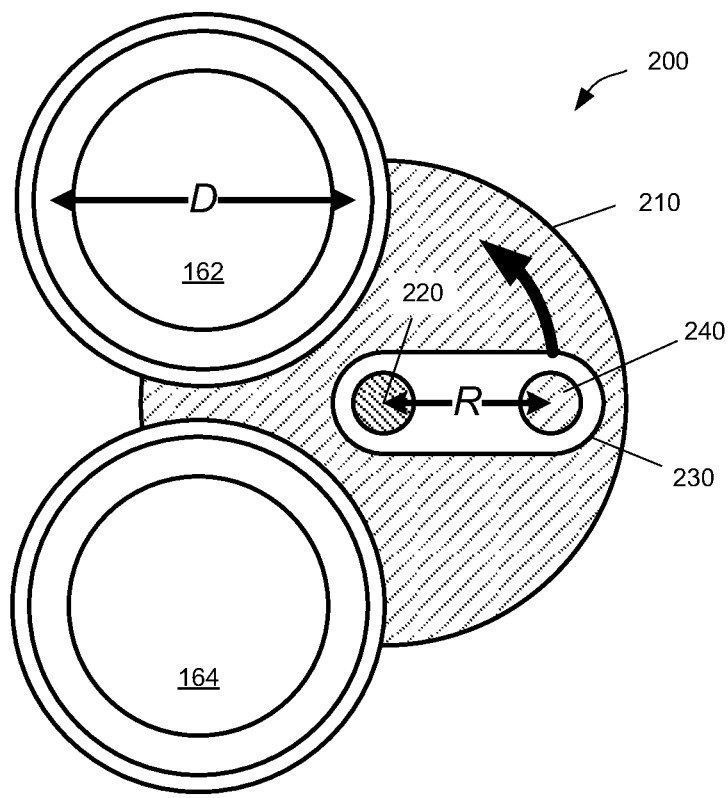
FIG. 2 depicts a shaking assembly for agitating an assay, according to some embodiments.

FIG. 2 depicts one embodiment of an agitator assembly 200 that may be included in an agitator 130. According to some implementations, an agitator 130 may comprise a motor 210 (e.g., stepper motor or induction motor) that rotates a motor shaft 220. In some implementations, the motor includes a geared transmission between a rotor of the motor and the shaft 220. The motor may rotate the shaft at speeds up to 2000 RPM. An armature 230 may be connected to the motor shaft and include a hole 240, pin, or other connecting feature that is spaced a distance R on center from a center of the motor shaft 220. In some embodiments, the hole 240 may be used to connect to a plate 132 of the agitator to which the sample wells 162, 164 can be secured. According to some embodiments, as the motor rotates, the plate and wells may be moved along an orbital trajectory having an orbital radius R. The orbital motion can induce mixing and agitation of solution in the wells.

The inventor has found that reducing the radius R of the shaker armature to dimensions on the order of the diameter D of the sample wells improves sensitivity of the immunoassay and reduces the amount of time during incubation of the biomarker in the capture and detection antibody mix. In some embodiments, a ratio of R:D is between about 1:2 and about 2:1. In some embodiments, a ratio of R:D is between about 1:1.25 and about 1.25:1. Other embodiments may use other ratios. In some implementations, a ratio of R:D is between about 1:7 and about 3:1. In some embodiments, a ratio of R:D is between about 1:6 and about 1:8. In some embodiments, a ratio of R:D is between about 1:1 and about 3:1. The rate of rotation of the motor shaft 220 may be between approximately 100 revolutions per minute (RPM) and approximately 1000 RPM. The rate of rotation may be dependent upon the diameter of the sample wells.

Figure 3A:
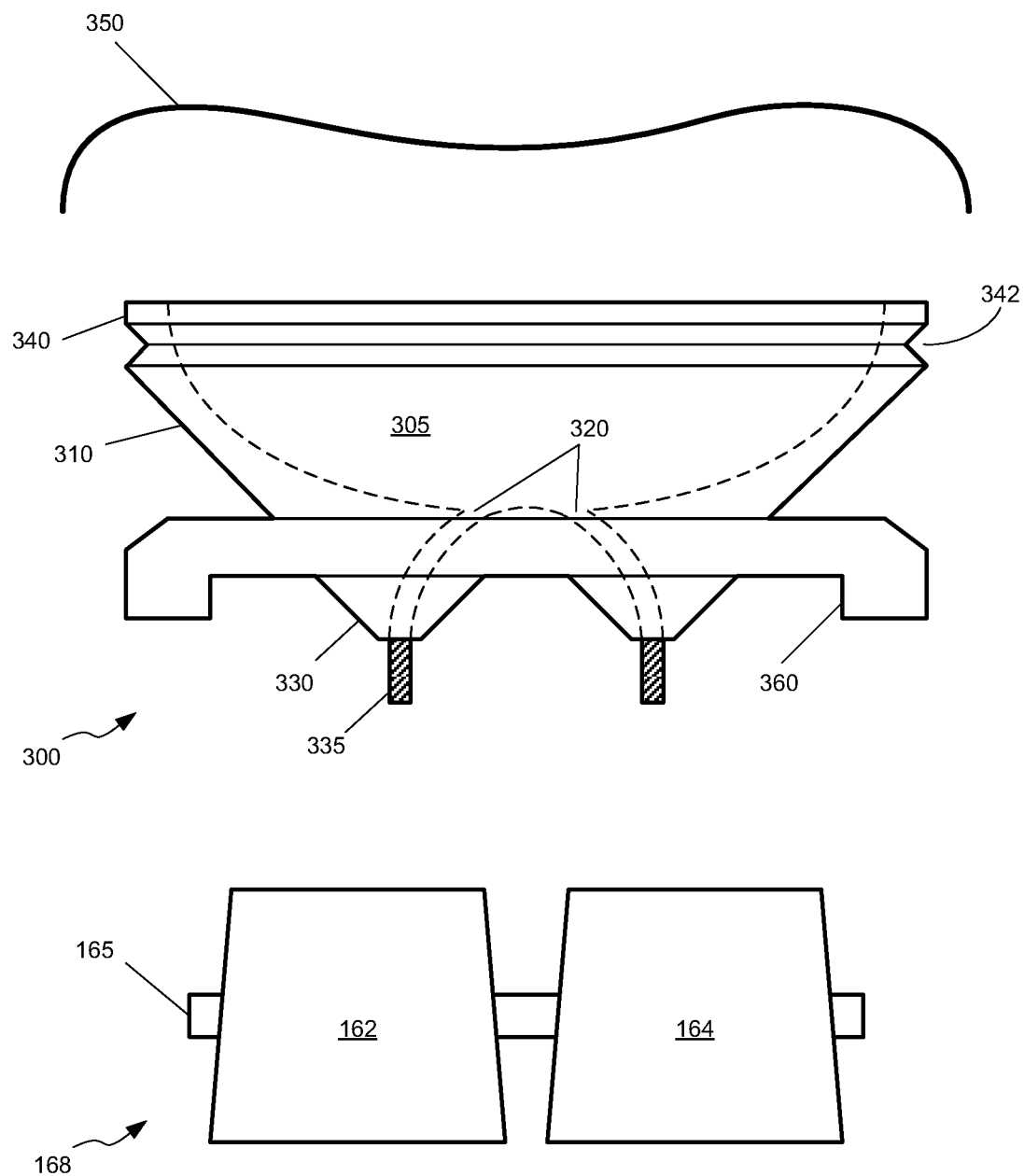
FIG. 3A depicts a multi-well funnel assembly that may be used to add a sample to assay wells, according to some embodiments.
Figure 3B:
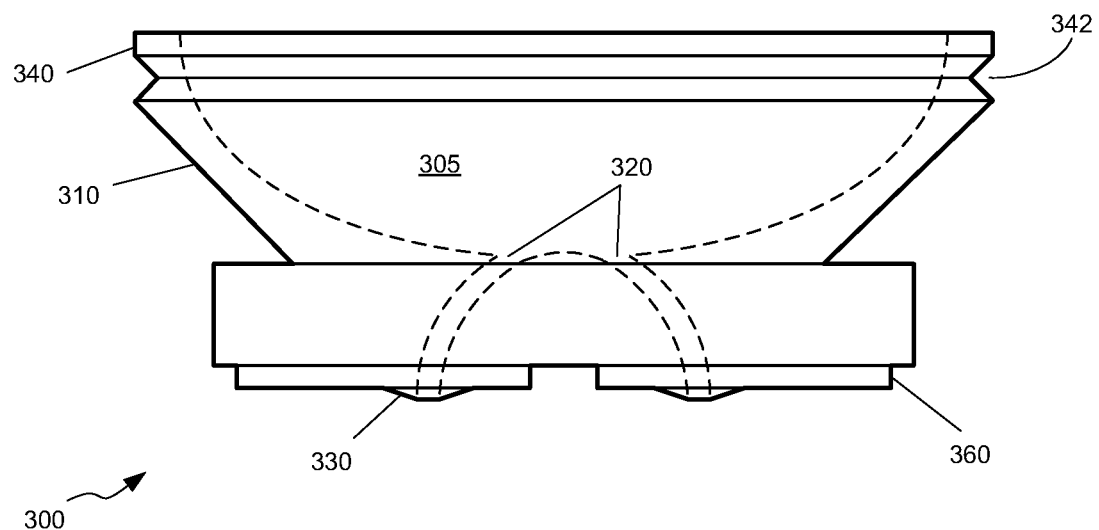
FIG. 3B depicts a multi-well funnel assembly that may be used to add a sample to assay wells, according to some embodiments.
Figure 3B:
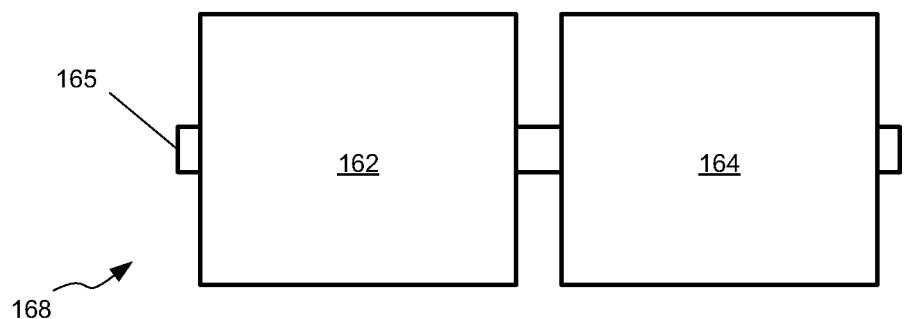

Just one example of sample wells and apparatus for loading samples into the sample wells is depicted in FIG. 3. The illustrated apparatus may be used in some embodiments. In some cases, a user may load a fluid sample into prepared sample wells 162, 164, and may use a funnel structure 310 to dispense the sample into the wells. In some instances, a membrane 350 may be used to filter a specimen (e.g., filter a blood sample to pass the plasma to the sample wells), so that the filtered component passes into the funnel and sample wells.

The sample wells 162, 164 may comprise disposable micro wells according to some embodiments. For example, the sample wells may be formed of a clear polymer in a continuous assembly where the wells are linked together through a linking structure 165 to form a sample well assembly 168. In some embodiments, the sample wells may be mounted in a sample well plate 160 that is received by the assay instrument. In some implementations, strip wells such as Costar 1×8 strips available from Sigma-Aldrich Co. LLC of St. Louis, Mo. may be used for the sample wells. The sample wells (and linking structure 165) may be formed of any suitable polymer including, but not limited to, polystyrene, polypropylene, polyethylene, acrylonitrile butadiene styrene (ABS), polyvinyl chloride (PVC), or nylon. In some embodiments, the polymer may be treated within the wells to allow for protein binding.

The sample wells may have any shape. In some implementations, an open top of the sample well may have a same or larger diameter than a bottom of the sample well, as depicted in FIG. 1A. In some implementations, an open top of the sample well may have a smaller diameter than a bottom of the sample well, as depicted in FIG. 3. The sample well shape depicted in FIG. 3 may be more suitable for agitating solutions in the samples wells during an incubation phase of the assay, while reducing the likelihood of spillage at higher agitation levels.

According to some embodiments, there may be only two sample wells included in a sample-well assembly 168 for an immunoassay. One well 164 may be used for a control assay to validate results from a test well 162, in which detection and quantification of a target biomarker or analyte is carried out. Additional sample wells (e.g., as many as eight) may be included in a sample-well assembly based on how many biomarkers are targeted for the assay (multiplex assay). In some embodiments, more than eight sample wells may be included in a sample-well assembly. In some embodiments, sample wells may be separate and mounted individually into a sample well plate 160.

In various embodiments, the sample wells are prepared prior to use with at least a capture binding agent (e.g., a capture antibody) that targets a particular biomarker of interest. For example, test wells 162 may be prepared by coating a bottom surface of test wells 162 with a target capture antibody directed against a target biomarker. Additionally, a bottom surface of control wells 164 may be coated with a control capture binding agent directed against a control protein or analyte, for example. Acts associated with preparation of the sample wells is described in further detail below.

Prepared sample wells may, in some embodiments, further include detection binding agents (e.g., detection antibodies). Detection binding agents may directed against the target biomarker in the test wells and against a control analyte in the control wells, for example. The inventor has found that both capture and detection binding agents (even when the detection binding agents are polyclonal antibodies) and conjugates for the detection binding agents can be included together in solution in prepared test wells before a biomarker and control analyte are added to the wells, and that detection and quantification of the target biomarker is still possible with high sensitivity. By combining capture and detection binding agents (as well as conjugates) into a prepared sample well before adding a sample, several lengthy incubation and wash steps associated with multi-step immunoassays, for example, can be eliminated. The combination of assay components can result in an appreciable reduction of time for the assay. Further aspects of an immunoassays are described below in connection with FIGS. 5A-5C.

In some embodiments, the prepared sample wells may be sealed (e.g., with a thin, transparent membrane) for subsequent transportation to a retailer and/or end user. A thin membrane may prevent contamination of the wells and extend the shelf life of the wells after preparation of the wells. The membrane may be removable by an end user.

Referring again to FIG. 3, a funnel structure 310 may be used to introduce a fluid sample, obtained from a human or animal, into plural sample wells simultaneously. The funnel may contain an upper wall 340 and a tapered lower body. The funnel structure may be formed from a polymer (e.g., any suitable polymer listed above for the sample wells), and may be disposable. An open, upper end of the funnel structure may be sealed with a thin membrane when manufactured to reduce risk of contamination. Alternatively, the funnel structure may be sterilized after manufacture and sealed in a sterile package. In some implementations, a funnel structure 310 may further include a registration features 360 that mechanically registers the funnel structure 310 to the sample wells 162, 164 and/or sample well assembly 168 to provide a stable assembly into which a fluid sample may be added. In some implementations, the registration features 360 may register to an interior of the sample wells, as depicted in FIG. 3B. For example, registration features 360 may fit inside the sample wells.

The upper wall of the funnel structure may include a groove 342 or other feature that may be used to attach a membrane 350 to a top of the funnel, for some implementations. For example, a filtration membrane may be loosely draped on the funnel and secured via an elastic that constricts into the groove 342. In some implementations, the elastic may be bonded to the membrane 350 at manufacture of the membrane, and delivered with the membrane. In some cases, a membrane may be placed on and packaged with the funnel. A fluid sample, when filtered by the membrane, or otherwise added to the funnel, may collect in a bowl region 305 of the funnel.

Many different patient sample types may be used with the portable instrument. In some embodiments, the sample type may be whole blood that may be filtered by the membrane 350. The membrane 350 may isolate a specific component of whole blood that is placed on top of the funnel and membrane. A large surface area of the membrane may aid in obtaining a desired amount of the specific blood component. A desired component of a whole blood sample may be serum or plasma. In another embodiment, the desired component may be red blood cells or hemoglobin. In another, the desired component may be lymphocytes or platelets. A filtered blood component may be channeled into one or more sample wells for testing.

In other embodiments, a sample other than whole blood may be used, and filtration may or may not be necessary. In some implementations, the sample type may be urine, amniotic fluid, or cerebrospinal fluid. In some cases, these samples may be directly added to the funnel structure without a membrane, and channeled into one or more sample wells for testing.

In some embodiments, samples may be added directly to the sample wells by a using a micropipette. In some cases, samples may be added to the funnel or samples wells via peristaltic pumps. Additionally or alternatively, samples may be added by a dispenser 140 of the instrument 100. For example, samples may be added via a disposable reservoir that is placed in the dispenser 140, and subsequently dispensed into the funnel or sample wells.

At the base of the bowl region 305 there may be plural channels 320 that drain the fluid sample substantially equally into two or more sample wells. A lower region of the funnel may or may not include protrusions 330 and/or tubes 335 that introduce the fluid sample into the sample wells. In some embodiments, the tubes 335 may punch through a thin membrane that seals the sample wells to reduce the risk of contamination or spillage of solutions in the sample wells. The membrane may be removed by the user prior to loading the sample wells into the portable assay instrument.

According to some embodiments, assay kits may be assembled that include any combination of the funnel structure, membrane, prepared sample wells, rinse solution, substrate solution, and stop solution. The prepared sample wells, rinse solution, substrate solution, and stop solution may be specific to a particular assay that targets a particular biomarker.

Figure 4:
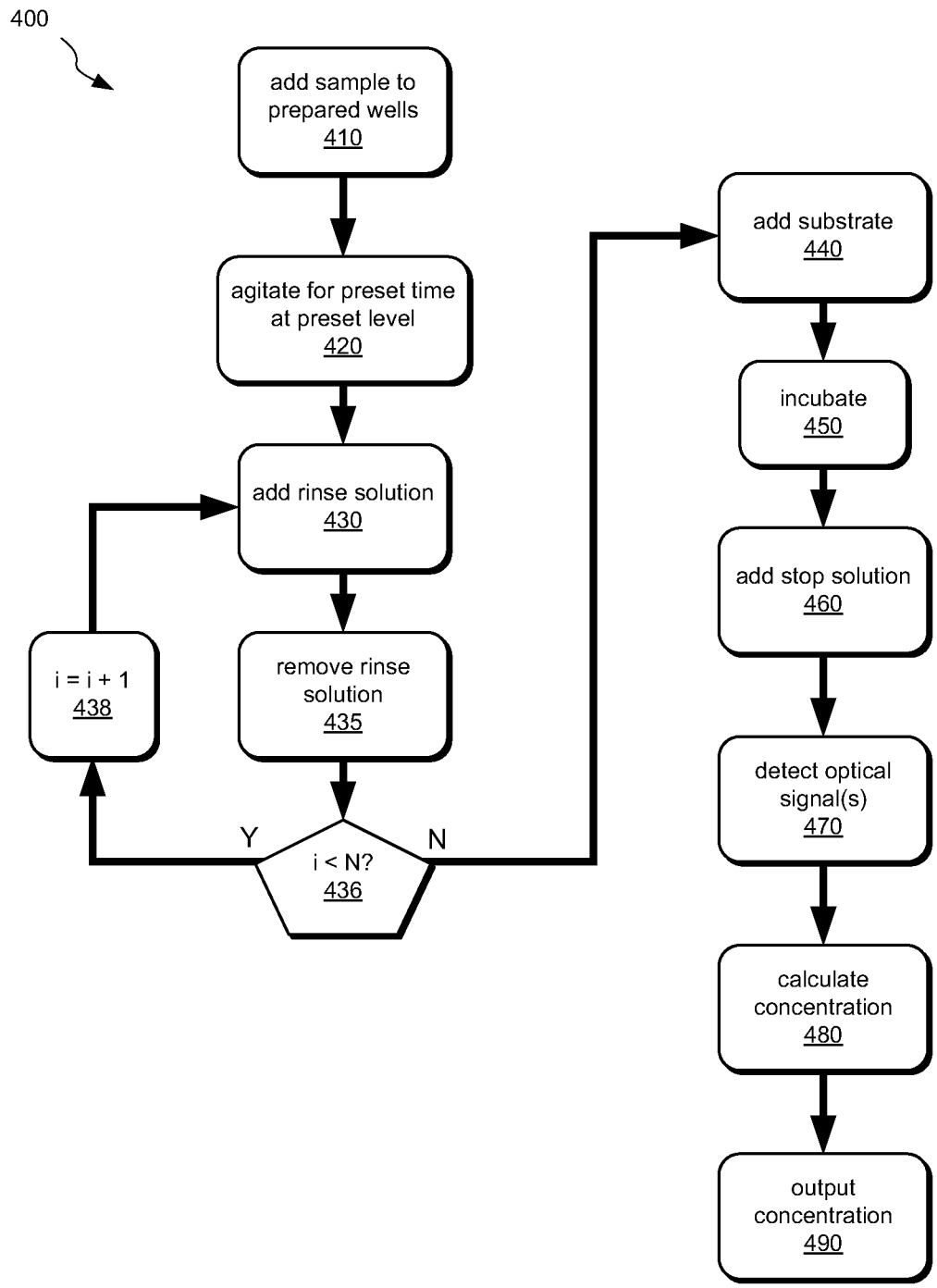
FIG. 4 illustrates acts of a method of operation of a portable instrument for in vitro detection and quantification of biomarkers, according to some embodiments.

An example method 400 for operating a portable assay instrument 100, 102 is illustrated by the flow diagram in FIG. 4. In some implementations, there may be additional or fewer acts than are depicted in FIG. 4. For example, acts of moving a sample plate from station to station may be included between some of the method steps.

According to one example, a method of operating a portable assay instrument may comprise adding 410 a sample that may contain a target biomarker to prepared sample wells. In some embodiments, a user may add the sample to the wells. In some implementations, the sample may be added to the sample wells by the instrument, e.g., dispensed from a vile or reservoir by a dispenser 140. The prepared sample wells may include an immobilizing binding agent and a detection binding agent. In some implementations, the prepared sample wells may further include a conjugate.

A method 400 of operating a portable assay instrument may comprise agitating 420 the sample in the prepared sample wells for a preset assay-specific agitation time. In some embodiments, the assay-specific time may be entered into the instrument by a user. In some implementations, the assay-specific time may be programmed into memory of the instrument. For example, assay-specific times may be stored in memory of the instrument in association with different types of assays that the machine is capable of performing. A user may identify to the instrument (e.g., select from a list of assays on a touch screen or via a user interface) a type of assay to be performed, and the instrument may automatically select the associated assay-specific agitation time from memory, and agitate the sample for the selected time. During the assay-specific agitation time, a sample suspected to contain a target biomarker may incubate with capture and detection binding agents in a sample well. Additionally, a detection conjugate may be present in the well. During agitation, the volume of solution in the sample wells may be less than 70% of the well volume to avoid spillage. In some embodiments, the volume of solution in the sample wells may be less than 50% of the well volume to avoid spillage.

A method of operating a portable assay instrument may comprise several (e.g., 1<N<8) cycles of adding 430 a rinse solution to the sample wells, and removing 435 the rinse solution from the sample wells. The rinse solution may be added to the wells by a dispenser 140 integrated with the instrument and controlled by a processor 105, and removed from the wells in any suitable manner. In some embodiments, a sample holder supporting the sample wells is rotated about an axis that is parallel to the solution surface in the wells to dump the solution from the wells. For example, the sample holder 120 may be moved to a dumping station, and the holder and sample plate 160 flipped by a motor to dump solution from the wells. According to some implementations, the sample plate 160 is rotated at a rate that maintains the solution in the wells until the plate is inverted and stopped. In this manner, solution may not intermix between the wells during the dumping action. In some embodiments, a high torque (standard size) servomotor (model ROB-11965) from Sparkfun Electronics of Niwot, Colo. is used to rotate the wells 180 degrees in approximately 0.5 seconds. In other embodiments, servomotors with more torque can be used to rotate the wells in even less time. In some implementations, the wells and well plate may be rotated approximately 180 degrees in time between approximately 0.1 seconds and approximately 0.7 seconds. In other embodiments, the solution may be aspirated from the wells using a suction pump and tubing introduced into the solution. In some embodiments, the number of rinsing cycles may be greater than 8.

In some embodiments, the instrument may rinse the sample wells using a multichannel micropipette. In some cases, peristaltic pumps may be used to add rinse solution to the sample wells. The rinse solution may comprise a buffered solution supplemented with a non-ionic detergent. For example, a wash buffer may comprise a solution of phosphate buffered saline (PBS) supplemented with Tween-20 or Triton X-100. In another embodiment, the wash buffer may comprise a solution of tris buffered saline (TBS) supplemented with Tween-20 or Triton X-100. The instrument may remove rinse solution from the wells in a decanting step where a motor rotates the sample well plate 180 degrees very rapidly several times. The amount of wash buffer added to the wells may fill between 25% and 110% of the total volume of the wells.

According to some embodiments, the acts of adding 430 and removing 435 rinse solution may be repeated a preset number of times N. In some embodiments, the value N may be any integer value between 1 and 10, and may be set by a user through a user interface of the instrument. Alternatively, values for N may be a pre-programmed, assay-specific values that are stored in a memory device of the instrument in association with assay types. When a user identifies an assay type to the instrument, an associated value for N may be recalled from the instrument's memory for that assay. Values for N may be determined from previous trials and minimized for an assay. During the rinsing steps, the instrument may increment 438 a counter value i, and determine 436 whether i is less than the preset value N as the instrument cycles through the rinsing steps.

When a preset number of rinsing steps has been performed, the assay instrument may add 440 substrate to the sample wells, and incubate 450 the wells and substrate for a substrate incubation period. According to some embodiments, the substrate may be added with the dispenser 140 by dispensing substrate from one or more substrate reservoirs, for example. In some embodiments, the incubation period may be between approximately 5 minutes and approximately 20 minutes duration, though shorter or longer durations may be used in other embodiments.

A method of operating a portable assay instrument may comprise adding 460 a stop solution to the wells. Stop solution may be added by a dispenser 140 by dispensing stop solution from one or more stop solution reservoirs, for example. Subsequently, an optical signal or signals may be detected 470 from the sample wells, and a concentration of a target biomarker may be calculated 480 based upon the detected optical signal or signals. The detection 470 may be repeated multiple times to obtain average signal values. A value of the calculated concentration may be output 490 to a display 170 associated with the instrument.

According to some embodiments, detection 470 of an optical signal may comprise detecting a color change and/or intensity of a color of a surface of the sample well at which an immobilization binding agent and target biomarker are located. In some implementations, a color change and/or intensity may be detected with a color-sensitive charge-coupled device (CCD) or complementary metal-oxide-semiconductor (CMOS) imaging array. Ambient light may be used to illuminate the sample wells during detection 470, in some embodiments. In some implementations, ambient light may excite fluorescence in a sample well that can be detected by a detector 155. Alternatively, light from an integrated light source 150 may be used to illuminate at least one sample well during detection 470. Detection 470 of an optical signal may comprise receiving, by a processor 105, a signal from an optical detector 155 that is representative of an amount of light form, or absorbance of light directed through, a sample well.

According to some embodiments, detection 470 may comprise detecting two signals at two different characteristic wavelengths from the sample wells. A light source may illuminate a test sample well 162 with radiation at a first characteristic wavelength that is less than about 500 nanometers (nm) and a second characteristic wavelength that is greater than about 500 nm. In some implementations, the first wavelength may be between about 350 nm and about 450 nm, and the second wavelength may be between about 550 nm and about 750 nm. One wavelength may be specific to the substrate used, e.g., absorbed strongly by the substrate, while the other wavelength may not be specific to the substrate, and is used as a control or correction signal. For example, if pNPP is used as the substrate in an assay, then a first absorbance value $A_s$ may be measure for a first light source emitting with a characteristic wavelength at approximately 405 nm. The characteristic wavelength may approximately equal a peak absorbance wavelength for pNPP. A second absorbance value $A_c$ may be measured for a second light source emitting with a characteristic wavelength at approximately 650 nm, which may serve as a control wavelength. According to some embodiments, the first absorbance value may be subtracted from the second absorbance value to determine an absorbance A for the sample well.

In some implementations, the two signals representative of optical intensity at two characteristic wavelengths and received from a detector 155 may be processed by a processor 105 to determine the absorbance $A_\lambda$ at each wavelength. The absorbance at each wavelength may be determined from the following expression $$A_\lambda = -\log\frac{I}{I_o}$$

where I is the detected intensity of light transmitted through a sample well and $I_0$ is an intensity of light incident on the sample well. $I_o$ may be measured by the same detector 155 prior to placing the sample wells between the light source 150 and detector, for example. According to some embodiments, absorbance for a sample well may be calculated by subtracting the absorbance determined for the substrate-specific wavelength from the absorbance determined for the control wavelength: $A=A_c-A_s$. In some implementations, a ratio of absorbance values may be used to determine an absorbance A.

In some implementations, detection 470 of an optical signal may comprise detecting a luminescent signal from a luminescent probe or species within the sample well. For example, a luminescent probe may be bound to any one of a capture binding agent, a target biomarker, or detection binding agent. In some cases, one of the capture binding agent, a target biomarker, or detection binding agent may fluoresce at a particular wavelength. Detection of a luminescent signal may indicate the presence and amount or absence of a target biomarker. For example, luminescence may be quenched when bound in a capture binding agent, biomarker, and detection binding agent sandwich, so that a reduction in luminescence may indicate the presence of a biomarker. In alternative embodiments, a luminescent probe may only remain in the well when a capture binding agent, biomarker, and detection binding agent are bound together, so that an increase in luminescence may indicate the presence of a biomarker. When a luminescent probe is used, a light source 150 may include a characteristic wavelength that is selected to efficiently excite the probe.

Regardless of how the detection is done, a calculated absorbance may then be used to determine a concentration of a target biomarker in a sample. For example, an absorbance A may be compared to pre-determined calibration data by a processor 105 to identify a concentration of the target biomarker in the sample. The pre-determined calibration data may be obtained using conventional assays and techniques, e.g., running known dilutions of biomarkers to obtain dose-response curves for the biomarkers.

Figure 5A:
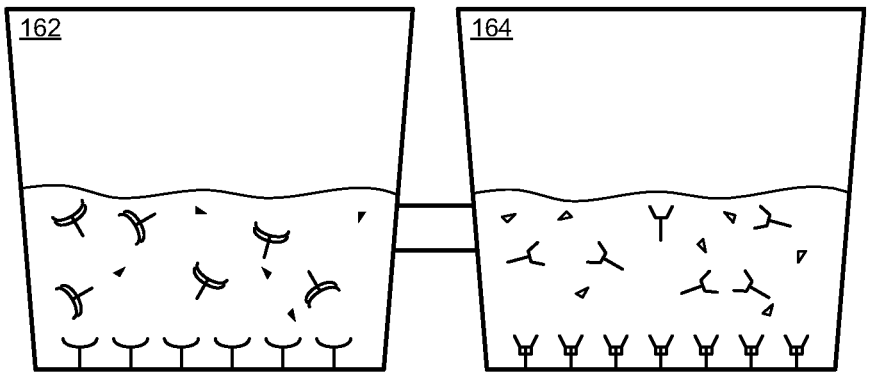
FIG. 5A depicts prepared sample wells containing capture analytes and detection analytes, according to some embodiments.
Figure 5B:
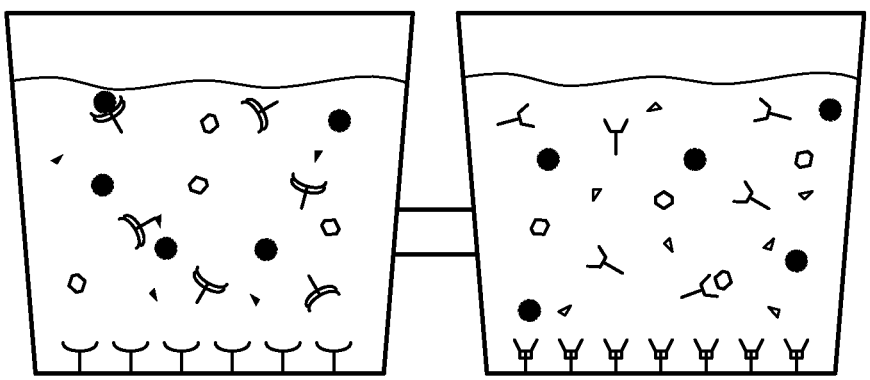
FIG. 5B depicts addition of a sample to prepared sample wells, according to some embodiments.
Figure 5C:
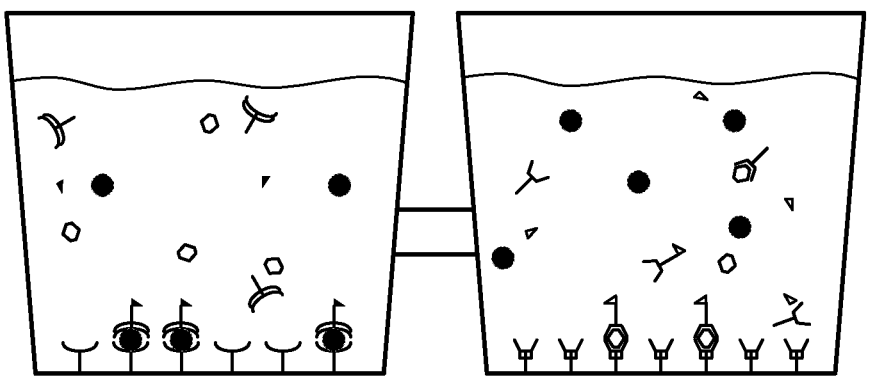
FIG. 5C depicts capture of target biomarkers and control analytes, according to some embodiments.

An example of an immunoassay that may be performed with a portable instrument 100 is depicted in FIGS. 5A-5C. An advantage of the assay depicted in FIGS. 5A-5C is that a target capture antibody 520, target biomarker 505, target detection antibody 510, and target conjugate 502 are all present in a sample well in one step during an incubation phase that captures and immobilizes the target biomarkers. Before introducing a sample suspected to contain a target biomarker, the target detection antibody 510, and target conjugate 502 are present in solution in the well along with the target capture antibody 520. Similarly, analogous control components may all be present in a control well during the same incubation phase. Although the immobilization and binding of the detection antibody and conjugate occur in a single incubation phase (during which the solutions are agitated) for this assay, other multi-step assays may be performed with the assay instrument. For example, the processor 105 may be programmed to run other assay sequences that include repetitions of acts shown in FIG. 4 and/or additional acts such as separate and sequential addition of a sample into wells prepared with only a capture binding agent, followed by addition of a detection antibody, incubation, addition of a conjugate, incubation, etc.

According to some embodiments, target components 502, 505, 510, 520 of a test immunoassay depicted in FIGS. 5A-5C are directed to a target biomarker 505 that may indicate an ailment in a human or animal. For example, a target biomarker (e.g., VEGF-C) may indicate renal transplant rejection or renal damage. Control components 532, 535, 540, 550 of a control assay may be directed to a control protein or substance that verifies that the test and control assays worked properly. One example of a control protein is human serum albumin (HSA). The test assay may be carried out in one or more test wells 162 and a control assay 164 may be carried out simultaneously in one or more control wells 164. In some implementations, some of the assay components may be the same for each well.

In some embodiments, the test and control wells may be prepared at a facility and shipped to an end user. For example, the prepared sample wells 162, 164, may be a consumable product that is purchased for single use. Prepared sample wells may appear as depicted in FIG. 5A, and comprise capture antibodies 520, 550 or capture binding agents, detection antibodies 510, 540 or detection binding agents, and may further include conjugates 502, 505 in solution. The solutions may only partly fill the wells, e.g., occupy less than one-half the volume of the wells. The wells may be sealed with a membrane.

The preparation of the wells prior to use may entail several steps. Non-limiting examples of preparation of sample wells will now be described. It will be appreciated that some of the steps may be used for preparing both test wells 162 and control wells 164. Preparation of test wells 162 may entail coating test wells with a target capture antibody 520 or binding agent directed against a human form of a biomarker 505 of interest. In some embodiments, control wells may be coated with a control capture antibody 550 directed against a human form of a control protein or biomarker 535.

In some embodiments, capture antibodies may be produced in animals, e.g., mouse, rat, or rabbit. In some embodiments, the capture antibodies may be produced in goat, sheep, guinea pig, horse, chicken, or duck. According to some embodiments, the capture antibodies may be monoclonal. In another embodiment, the capture antibodies may be polyclonal. In some implementations, capture antibodies for a test well may be a combination of both polyclonal and monoclonal antibodies.

Coating of the sample wells with capture antibodies or binding agents may be done for an extended period of time (e.g., between about 6 and 12 hours) at room temperature. In some implementations, coating may be performed at temperatures between about 4° C. and about 25° C. The coating can also be done for less time or more time in other embodiments.

Following the coating, the sample wells may be washed with a wash buffer. In some implementations, the sample wells may be partially filled with a buffer. The wash buffer may comprise a solution of phosphate buffered saline (PBS) supplemented with a non-ionic detergent such as Tween-20 or Triton X-100. In another embodiment, the wash buffer may comprise a solution of TBS (tris buffered saline) instead of PBS. The wash step could be repeated anywhere from one to six times to remove excess antibodies or binding agents from the wells.

Following washing, the sample wells may be blocked with a blocking agent to prevent non-specific binding to the sides of the sample wells. In one embodiment, the blocking agent may comprise a solution of bovine serum albumin (BSA). In another embodiment, the blocking agent may comprise a casein-based solution or a solution of non-fat dry milk. Other blocking agents may be used additionally or alternatively. The blocking agent may form a passivating film (not shown in the drawings) on the interior surfaces of the sample wells. The blocking agent may be incubated for a period of time similar to the capture antibody, and a sequence of wash steps may be repeated one to six times to remove excess blocking agent from the wells.

A target detection antibody 510 or binding agent directed against the target biomarker 505 may be diluted to a predetermined concentration and placed in the test sample wells 162. In some embodiments, the predetermined concentration ranges may be between approximately 10 micrograms/milliliter (µg/mL) and approximately 1 nanogram/milliliter (ng/mL). A control detection antibody 540 directed against the control protein or biomarker 535 may be diluted to a predetermined concentration and placed into the control sample wells 164.

According to some embodiments, a common detection conjugate may be added to both test and control wells. For example, the detection antibodies may be labeled with biotin and the detection conjugate may be streptavidin or avidin conjugated to an enzyme such as horseradish peroxidase (HRP).

In another embodiment of the invention, the detection antibodies are non-labeled and the detection conjugate may be an anti-IgG antibody conjugated to HRP or alkaline phosphatase (AP) and directed against the Fc region of the detection antibodies. For example, if the detection antibodies were produced in a rabbit, then the conjugate may be a goat anti-rabbit antibody directed against the Fc region of the rabbit antibody.

In some embodiments, detection antibodies and/or detection conjugates are produced in mouse, rat, or rabbit. In some embodiments, detection antibodies and/or detection conjugates are produced in goat, sheep, guinea pig, horse, chicken, or duck. In some embodiments, detection antibodies and/or detection conjugates are monoclonal and in other embodiments they are polyclonal. In some implementations, detection antibodies and/or detection conjugates are a combination of both polyclonal and monoclonal antibodies. In some embodiments, an enzyme used as a conjugate is horseradish peroxidase, and in some cases the enzyme is alkaline phosphatase. Other enzymes that can catalyze the conversion of substrate into a product with a visible color and/or optical absorbance may be used additionally or alternatively.

According to some implementations, assay components in prepared wells may be diluted in stability buffers to preserve and/or enhance their activity over time. Stability buffers may increase the shelf life of the prepared sample wells, so that they may be function in an at-home or clinical setting. In one embodiment of the invention, a stability buffer (product #: 131000) from Boca Scientific of Boca Raton, Fla. is used. Accordingly, the sample wells are ready for use and may then be sealed for delivery to an end user.

Referring now to FIG. 5B, once the patient samples have been added to the sample wells, the assay may be incubated to capture the target biomarkers if present. During this incubation phase, the sample wells may be agitated (e.g., shaken with a small radius of orbit for a duration between 1 and 30 minutes by an agitator 130) to accelerate the incubation. The biomarkers may begin to bind to the antibodies in the sample wells and diffuse towards the bottom of the wells where they may be immobilized by the capture antibodies, as depicted in FIG. 5C. Subsequent rinsing leaves behind only the bound material at the bottom of the wells. A negative result for a test well may have no bound material at the bottom of the wells.

Although FIGS. 5A-5C depict an assay for detecting and quantifying a single biomarker, in other embodiments multiple biomarkers may be screened (multiplex assay) in an assay run with the instrument by increasing the number of test wells to include other wells with different target components.

After the incubation and rinsing phases are completed, substrate may be added to the sample wells, followed by addition of a stop solution. If an enzyme used in an assay is alkaline phosphatase, then a possible substrate may be (4-nitrophenyl) dihydrogen phosphate (pNPP). The substrate may be incubated in the wells with the substrate for anywhere from 10 to 30 minutes depending on the intensity of the substrate selected. A type of stop solution depends on the substrate used. In some embodiments, the stop solution may comprise sodium hydroxide (NaOH). In some implementations, the stop solution may comprise sulfuric acid ($H_2SO_4$).

Any of the rinse solutions, buffers, sample, substrate, and stop solutions may be added to the sample wells using a micropipette or peristaltic pumps. For example, a solution may be added by dispenser 140 using a peristaltic pump and micropipette.

Other combinations of assay components may be used in other embodiments to detect the same or different biomarkers. Alternative assay components are described below.

Immunoassays/ELISAs

In some embodiments, an enzyme-linked immunosorbent assay (ELISA) provided herein is used to identify specific substances, such as peptides, proteins, antibodies, and hormones, using antibodies and different detection techniques in clinical diagnostic testing and biological research. In some embodiments, the ELISA results in a colored end product which correlates with the amount of analyte present in the sample and can be quantified with the use of a standard curve. In some embodiments, the assay is performed in a multi-well cartridge or plate, where a particular binding agent is immobilized to a solid surface and then complexed with an antibody linked to an enzyme. In some embodiments, the conjugated enzyme is incubated with a substrate, producing a color change, and the enzyme-substrate reaction is measured accordingly. In some embodiments, the ELISA is a one-step ELISA, in which the well is pre-coated with a binding agent (e.g., a primary antibody) and the sample and the antibody's substrate (target antigen) are added to the well to obtain a signal.

In some embodiments, the ELISA results are quantitative. For example, in some embodiments, measurement data can be interpreted in comparison to a standard curve (a serial dilution of a known, purified antigen) to precisely calculate the concentrations of antigen in the samples. In other embodiments, the ELISA can be used to qualitatively compare whether or not the antigen or antibody is present in the sample. In other embodiments, ELISA results can be used to compare the relative levels of antibodies or antigens in different samples based on the variation in signal intensity. In some embodiments, an ELISAs is used to detect the present of illicit drugs or metabolites thereof in a sample. However, in some embodiments, ELISAs are used to diagnose human immunodeficiency virus (HIV), lyme disease, pernicious anemia, Rocky Mountain spotted fever, rotavirus, squamous cell carcinoma, syphilis, toxoplasmosis, hepatitis C, hepatitis B, HTLV-1, and varicella zoster virus, among others. In some embodiments, ELISAs are used to detect pathogens in a sample. In some embodiments, ELISAs is used to detect the present of illicit drugs or metabolites thereof in a sample. In some embodiments, ELISAs are used to detect a biomarker associated with a disease (e.g., cancer) or other condition (e.g., organ rejection).

Immunoassay Binding Agents

In some embodiments, monoclonal or polyclonal antibodies or fragments thereof are used as binding agents in an immunoassay, e.g., an ELISA, provided herein. In some embodiments, the antibody has an affinity for the antigen so that it binds the substance at the exclusion of other substances present in the sample. In some embodiments, the three-dimensional configuration of the antigen-binding site of a Fab portion of the antibody controls the strength and specificity of its interaction with the antigen. In some embodiments, the stronger the interaction between antigen and antibody, the lower the concentration of antigen that can be detected in the assay.

As used herein, the term antibody refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

As used herein, the term antibody fragment refers to any derivative of an antibody which is less than full-length. Preferably, the antibody fragment retains at least a significant protion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

In some embodiments, single-chain Fvs (scFvs) may be used as binding agents. ScFvs are recombinant antibody fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

In some embodiments, diabodies may be used as binding agents. Diabodies are dimeric scFvs. The components of diabodies typically have shorter peptide linkers than most scFvs, and they show a preference for associating as dimers.

In some embodiments, Fv fragments may be used as binding agents. An Fv fragment is an antibody fragment which consists of one VH and one VL domain held together by noncovalent interactions. The term dsFv is used herein to refer to an Fv with an engineered intermolecular disulfide bond to stabilize the VH-VL pair.

In some embodiments, F(ab')2 fragments may be used as binding agents. A F(ab')2 fragment is an antibody fragment essentially equivalent to that obtained from immunoglobulins (typically IgG) by digestion with an enzyme pepsin at pH 4.0-4.5. The fragment may be recombinantly produced.

In some embodiments, Fab fragments may be used as binding agents. A Fab fragment is an antibody fragment essentially equivalent to that obtained by reduction of the disulfide bridge or bridges joining the two heavy chain pieces in the F(ab')2 fragment. The Fab' fragment may be recombinantly produced.

However, in some embodiments, non-immunoglobulin molecules may be used as binding agents. For example, aptamers, antigen binding ligands or receptors, etc.

Immunoassay Detection Agents

In some embodiments, horseradish peroxidase (HRP) or alkaline phosphatase (AP) are used to directly detect an enzymatic signal. Many substrates are available for performing ELISAs with HRP and AP, which may conjugated to detection agents. In some embodiments, other enzymes, such as β-galactosidase, acetylcholinesterase, and catalase are used. In some embodiments, the agents are bound to secondary antibodies and produce a colormetric signal which is readable by a spectrophotometer or other optical device. In an alternative embodiment, detection can occur with the use of fluorescently-labeled antibodies (fluorescence-linked immunosorbent assay (FLISA)).

In other embodiments, detection is indirect. The antibodies are coupled to biotin, a small and stable label, which then binds with high affinity to a streptavidin-conjugated enzyme. If unlabeled primary antibodies are used, an enzyme-coupled or biotinylated secondary antibody is useful. If the secondary antibody is biotinylated, then it is useful to administer a streptavidin-enzyme conjugate and then the appropriate substrate for detection purposes.

Transplant Rejection

In some embodiments, an immunoassay disclosed herein can be used to identify or detect organ or other transplant rejection. In some embodiments, the transplant encompasses one or more of the following: heart, kidney, liver, lung, pancreas, intestine, cornea, bone, heart valve, skin, and blood vessels.

Transplant rejection occurs when transplanted tissue is rejected by the recipient's immune system, ultimately destroying the transplanted tissue. In some embodiments, rejection occurs via the adaptive immune response, which is mediated by killer T cells and induces the apoptosis of target cells, humoral immunity, which is mediated by activated B cells secreting antibody molecules, and the innate immune response, which includes the phagocytes and soluble immune proteins and activates the complement cascade, resulting in cell death. There are three types of rejection: hyperacute rejection, acute rejection, and chronic rejection. Hyperacute rejection occurs within minutes of the transplant, resulting from preexisting humoral immunity and leading to systemic inflammatory response syndrome. As a result, the transplanted tissue must be removed. Acute rejection is caused by cellular immunity and occurs within the months and years following the transplant. It is usually treated with immunosuppressive drugs, including corticosteroids (such as prednisolone and hydrocortisone), calcineurin inhibitors (such as cyclosporin and tacrolimus), antiproliferatives (such as azathioprine and mycophenolic acid), and mTOR inhibitors (such as sirolimus and everolimus).

Antibody-based treatments are also used in conjunction with immunosuppressive therapy, including monoclonal anti-IL-2Rα receptor antibodies, polyclonal anti-T-cell antibodies, and monoclonal anti-CD20 antibodies. Bone marrow transplants have also been used to replace the transplant recipient's immune system with that of the donor; however, there is a risk of graft-versus-host disease as mature lymphocytes may enter the marrow and destroy the new host tissues. Chronic rejection is the long-term loss of function of a transplanted organ, usually due to fibrosis of the transplanted organ's blood vessels, and is usually treated with a new transplant. Thus, in some embodiments, immunoassays disclosed herein are useful for detecting biomarkers associated with organ and/or transplant rejection.

In some embodiments, biomarkers associated with kidney transplant rejection, a leading cause of end-stage renal disease, can be detected by an immunoassay disclosed herein. In some embodiments, one or more of the following biomarkers may be detected using immunoassays disclosed herein for assessing kidney transplant rejection: vascular endothelial growth factor-C (VEGF-C), integrin α3, integrin α4, soluble vascular cell adhesion molecule 1 (sVCAM-1), vascular cell adhesion molecule-1 (VCAM-1), and anti-intercellular adhesion molecule-1 (ICAM-1), transforming growth factor beta (TGF-β), and monocyte chemotactic peptide-1 (MCP-1/CCL2).

Cancer

In some embodiments, an immunoassay can be used to detect a biomarker indicative of diseases such as cancer. For example, an immunoassay disclosed herein can be used to detect a biomarker associated with one or more of the following cancers: colon carcinoma, pancreatic cancer, breast cancer, ovarian cancer, prostate cancer, squamous cell carcinoma, cervical cancer, lung carcinoma, small cell lung carcinoma, bladder carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, bile duct carcinoma, choriocarcinoma, seminoma, embryonal carcinoma, or testicular cancer. In certain embodiments, the cancer is a breast carcinoma or a lung carcinoma.

In some embodiments, the cancer detected is ovarian cancer. Ovarian cancer is a heterogeneous and rapidly progressive disease of low prevalence and poor survival. It represents the fifth leading cause of cancer-related deaths in American women. It is the most lethal gynecological malignancy, accounting for more deaths than endometrial and cervical cancer combined, mainly due to the lack of highly sensitive or specific screening tools for the early detection of early-stage disease, such as biomarkers. In some embodiments, VEGF proteins (e.g., VEGF-C) and CA-125, a glycoprotein antigen are biomarkers useful for detecting epithelial ovarian tumors. In addition, mesothelin, transthyretin (TTR), and ApoA1 are also candidate biomarkers for early ovarian cancers.

EXAMPLES

Figure 6:
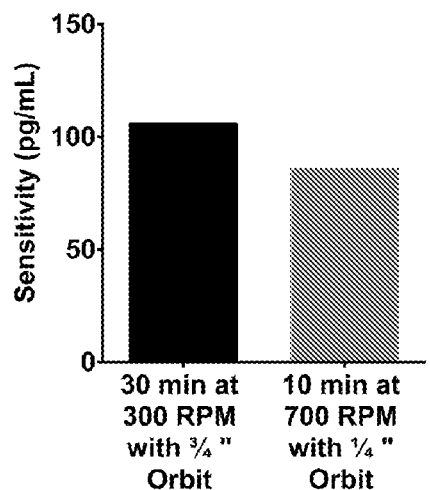
FIG. 6 illustrates a change in assay sensitivity dependent on agitation conditions.

Several procedures were carried out with a prototype assay instrument 100. In a first procedure, agitation conditions were varied to evaluate assay sensitivity dependence. It was found that sensitivity of the assay can be improved with increased agitation. An example result is shown in FIG. 6. In this procedure, the sample wells were agitated with an orbital shaking assembly, such as depicted in FIG. 2. A length of an armature 230 of the shaker was varied to change an orbital radius R of the shaker. For each case, the speed of the shaker was increased to a value that provided a highest level of agitation without spillage of solution from the wells. At smaller radius values, the speed of the shaker could be increased without resulting in spillage of solution. Additionally, for each case, the amount of time in the shaker was varied to provide a lowest sensitivity of the assay.

With a larger orbital radius R of approximately 19 mm, the shaker could be operated at a speed of 300 revolutions per minute (RPM) without spillage of solution from the wells. A sensitivity for the assay after 30 minutes of incubation with agitation was found to be approximately 105 picograms/milliliter (pg/mL). With a smaller orbital radius of approximately 12 mm, the shaker could be operated at a speed of 700 revolutions per minute (RPM) without spillage of solution from the wells. A sensitivity for the assay after 10 minutes of incubation with agitation was found to be approximately 86 picograms/milliliter (pg/mL). From these results, the increased agitation conditions reduced an incubation-time-sensitivity product by more than 70%. This was an unexpectedly large improvement in assay performance for the change in agitation conditions.

It may be appreciated that agitation conditions can be trialed for different types of assays in optimization experiments, so that assay-specific agitation times (e.g., incubation times under agitation) and conditions (e.g., levels of agitation) can be determined for each assay type. The automated assay instrument is useful for running such optimization experiments, since all steps of an assay can be automated. Once determined, the assay-specific agitation times and conditions may be programmed into a portable assay instrument (e.g., at a manufacturing facility).

Figure 7:
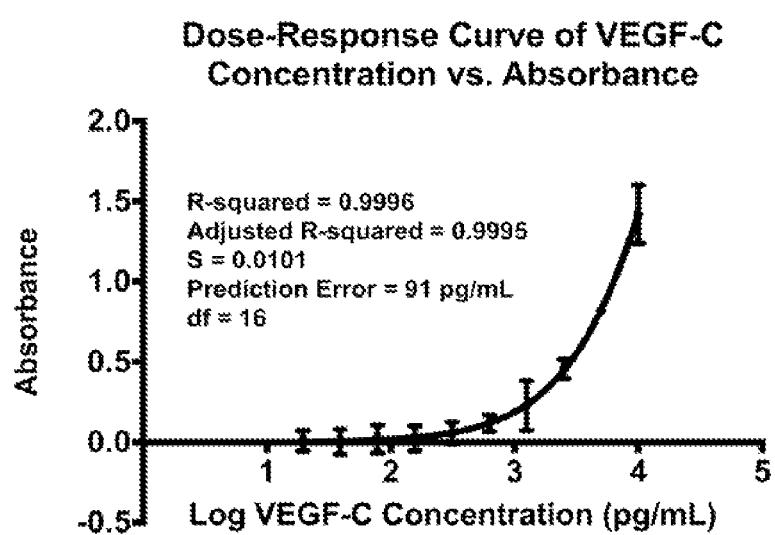
FIG. 7 illustrates a dose-response curve measured for VEGF-C using a portable instrument for in vitro detection and quantification of biomarkers.

In a separate procedure, the prototype instrument 100 was used to quantify the concentration of the biomarker VEGF-C in calibration solutions. An assay for detecting and quantifying VEGF-C in human serum samples may be used to detect chronic transplant rejection in renal recipients. Spike and recovery assays were first run to identify a diluent that would accurately mimic a human serum sample. The results of these assays showed that a diluent of 10% fetal bovine serum (FBS) in buffered saline accurately mimicked human serum samples. This diluent was used for dose-response tests with the biomarker VEGF-C. Serial dilutions of VEGF-C in the diluent were then assayed using the prototype instrument, and absorbance values A were recorded for each dilution. The results of the measurements are plotted in FIG. 7.

For the assays, sample wells were prepared as described in connection with FIG. 5A. The immobilized binding agent in the prepared sample wells was anti-VEGF-C capture antibody. The well surfaces were blocked with bovine serum albumin (BSA). The detection binding agent was biotinylated detection antibody, and the conjugate was streptavidin-HRP. The anti-VEGF-C capture antibody, biotinylated detection antibody, and streptavidin-HRP were all present in the prepared test sample wells 162 prior to addition of biomarker dilutions.

Immediately after adding a dilution of VEGF-C to the sample wells, the wells were incubated in the agitator for approximately 10 minutes. After rinsing the wells, a TMB ELISA substrate (catalog number: ab171527) from Abcam of Cambridge, Mass. was added to the wells and incubated for approximately 15 minutes. A dilution of sulfuric acid was then used to stop the reaction. Absorbance measurements were made by the prototype instrument as described above.

The measured absorbance values were fit to a four-parameter logistic curve (4-PL), yielding an $R^2$ value of 0.9996 and a prediction error of 91 pg/mL. The measured absorbance values did not saturate at high concentrations, indicating that an even larger dynamic range of VEGF-C concentrations can be accurately assayed by the instrument.

A standard ELISA sensitivity assay was also run to determine the minimum detectable concentration (MDC) of VEGF-C that could be detected by the prototype instrument. Nine absorbance measurements (log values) for nine standard zero replicates (samples not containing VEGF-C) were averaged and plotted along with the determined dose-response curve. An upper limit of the confidence interval for the null tests indicated an assay sensitivity for the VEGF-C biomarker of 66 pg/mL.

Conclusion

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., automation of a portable assay instrument, may be embodied at least in part as a computer-readable storage medium (or multiple computer readable storage media) (e.g., a computer memory, one or more floppy discs, compact discs, optical discs, magnetic tapes, flash memories, or other tangible computer storage medium or non-transitory medium) encoded with one or more programs that, when executed on one or more computers or other processors, perform methods that implement the various embodiments of the technology discussed above. In some implementations, aspects of the invention may be embodied as circuit configurations in Field Programmable Gate Arrays or other semiconductor devices. The computer readable medium or media can be transportable, such that the program or programs stored thereon can be loaded onto one or more different computers or other processors to implement various aspects of the present technology as discussed above.

The terms "program" or "software" may be used to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The term "associated with," when used in connection with data structures, may be used to describe a combination of data structures in some embodiments. For example, first data associated with second data may mean adding the first data to a data record containing the second data, or vice versa. "Associated with" may mean establishing a relational data structure between first and second data in some embodiments. For example, first data may be entered in a table or augmented with an identifier that cross-references or links the first data to second data, even though the first and second data may be stored in different data stores.

The terms "about," "approximately," and "substantially" may be used to refer to a value, and are intended to encompass the referenced value plus and minus variations that would be insubstantial. The amount of variation could be less than 5% in some embodiments, less than 10% in some embodiments, and yet less than 20% in some embodiments. In embodiments where an apparatus may function properly over a large range of values, e.g., one or more orders of magnitude, the amount of variation could be a factor of two. For example, if an apparatus functions properly for a value ranging from 20 to 350, "approximately 80" may encompass values between 40 and 160.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method for detecting and quantifying a target biomarker with an integrated instrument, the method comprising:
   receiving a single-use and disposable prepared sample well in a sample holder of the integrated instrument, wherein prior to being received in the sample holder the single-use and disposable prepared sample well is sealed to contain:
   an immobilized binding agent specific to the target biomarker;
   a detection binding agent specific to the target biomarker in a solution;
   a blocking solution comprising at least one of bovine serum albumin (BSA) and non-fat dry milk; and
   a stability buffer capable of preserving and enhancing assay components over time;
   receiving a sample in the sample well, wherein the sample comprises the target biomarker;
   automatically agitating the sample well at an agitation station of the integrated instrument; detecting radiation from the sample well with a detector of the integrated instrument; and quantifying a concentration of the target biomarker based on the detected radiation from the sample well wherein the agitation period is less than 10 minutes and wherein a time from initiation of agitation and calculation of the target biomarker concentration is no greater than 30 minutes.

2. The method of claim 1, wherein the prepared sample well is sealed with a membrane.

3. The method of claim 1, further comprising removing a seal from the prepared sample well prior to receiving the prepared sample well in the sample holder.

4. The method of claim 1, wherein the capture binding agent is an antibody.

5. The method of claim 1, wherein the detecting binding agent is an antibody.

6. The method of claim 1, wherein the blocking solution comprises a casein-based solution.

7. The method of claim 1, where detecting radiation from the sample well comprises measuring an optical property of the sample well with an optical detector of the integrated instrument.

8. The method of claim 7, wherein the optical property is a wavelength of light.

9. The method of claim 7, wherein the optical property is intensity of light.

10. The method of claim 7, wherein the optical property is fluorescence.

11. The method of claim 7, wherein the optical property is absorbance of light.

12. The method of claim 11, further comprising illuminating the sample well with light at a first characteristic wavelength and light at a second characteristic wavelength that is different from the first characteristic wavelength, wherein quantifying a concentration of the target biomarker comprises comparing a first absorbance value detected for the first characteristic wavelength and second absorbance value for the second characteristic wavelength.

13. The method of claim 12, wherein quantifying a concentration of the target biomarker comprises subtracting the first absorbance value from the second absorbance value.

14. The method of claim 12, wherein the target biomarker indicates chronic transplant rejection or cancer.

* * * * *